(12) United States Patent
Rachlin et al.

(10) Patent No.: US 7,931,596 B2
(45) Date of Patent: Apr. 26, 2011

(54) ULTRASOUND INTERFACING DEVICE FOR TISSUE IMAGING

(75) Inventors: Daniel Rachlin, San Jose, CA (US); Stanley R. Conston, San Carlos, CA (US)

(73) Assignee: Iscience Interventional Corporation, Menlo Park, CA (US)

( * ) Notice: Subject to any disclaimer, the term of this patent is extended or adjusted under 35 U.S.C. 154(b) by 87 days.

(21) Appl. No.: 10/521,045

(22) PCT Filed: Jul. 14, 2003

(86) PCT No.: PCT/US03/21899
§ 371 (c)(1), (2), (4) Date: Jan. 11, 2005

(87) PCT Pub. No.: WO2004/006774
PCT Pub. Date: Jan. 22, 2004

(65) Prior Publication Data
US 2005/0240102 A1      Oct. 27, 2005

(51) Int. Cl.
*A61B 5/05* (2006.01)
*A61B 8/00* (2006.01)
*A61F 9/00* (2006.01)

(52) U.S. Cl. ......... 600/459; 606/107; 600/452; 600/444

(58) Field of Classification Search ........... 600/459–471
See application file for complete search history.

(56) References Cited

U.S. PATENT DOCUMENTS

| | | | |
|---|---|---|---|
| 3,371,660 A * | 3/1968 | Carlin ........................... | 600/452 |
| 3,939,123 A | 2/1976 | Matthews et al. | |
| 4,118,354 A | 10/1978 | Harada et al. | |
| 4,120,291 A * | 10/1978 | Paton et al. ..................... | 73/620 |
| 4,209,605 A | 6/1980 | Hoy et al. | |
| 4,483,343 A | 11/1984 | Beyer et al. | |
| 4,644,033 A | 2/1987 | Gnanou et al. | |
| 4,649,925 A | 3/1987 | Dow et al. | |
| 4,722,346 A | 2/1988 | Chen | |
| 4,796,632 A | 1/1989 | Boyd et al. | |
| 4,823,801 A * | 4/1989 | Sakane ......................... | 600/452 |
| 4,867,169 A | 9/1989 | Machida et al. | |
| 4,911,173 A * | 3/1990 | Terwilliger ................... | 600/464 |
| 5,078,149 A | 1/1992 | Katsumata et al. | |

(Continued)

OTHER PUBLICATIONS

Mesh. (n.d.). The American Heritage® Dictionary of the English Language, Fourth Edition. Retrieved May 19, 2009, from Dictionary. com website: http://dictionary1.classic.reference.com/browse/mesh.*

*Primary Examiner* — Long V. Le
*Assistant Examiner* — Helene Bor
(74) *Attorney, Agent, or Firm* — GSS Law Group; James J. Leary; Carol D. Titus

(57) ABSTRACT

A device (10) used with high frequency ultrasound provides a replaceable barrier between the ultrasound transducer and the tissues being imaged. The device (10) provides an acoustic pathway of minimal effect on the ultrasound signals, and furthermore provides for a safety barrier between a mechanical scanner and the tissues being imaged. The configuration of the device (10) allows it to function as a standoff for the ultrasound transducer to place the focus of the ultrasound beam at the desired depth of tissue for imaging. In addition, the device (10) may be sterilized and replaced as needed, providing sterile tissue contact surfaces. The device (10) has additional features, which are especially advantageous for diagnosis and surgery of the eye.

25 Claims, 2 Drawing Sheets

Perspective drawing of the ultrasound transducer interface

U.S. PATENT DOCUMENTS

| Patent No. | | Date | Inventor(s) | Class |
|---|---|---|---|---|
| 5,165,415 A | * | 11/1992 | Wallace et al. | 600/452 |
| 5,175,229 A | | 12/1992 | Braatz et al. | |
| 5,293,871 A | * | 3/1994 | Reinstein et al. | 600/442 |
| 5,331,962 A | * | 7/1994 | Coleman et al. | 600/444 |
| 5,357,963 A | * | 10/1994 | Mayol et al. | 600/446 |
| 5,369,454 A | * | 11/1994 | Reinstein et al. | 351/201 |
| 5,400,785 A | * | 3/1995 | Crowley | 600/467 |
| 5,494,038 A | * | 2/1996 | Wang et al. | 600/459 |
| 5,551,432 A | * | 9/1996 | Iezzi | 600/445 |
| 5,575,291 A | * | 11/1996 | Hayakawa et al. | 600/459 |
| 5,626,554 A | | 5/1997 | Ryaby et al. | |
| 5,770,801 A | | 6/1998 | Wang et al. | |
| 5,776,068 A | * | 7/1998 | Silverman et al. | 600/443 |
| 5,834,687 A | * | 11/1998 | Talbot et al. | 174/386 |
| 5,840,023 A | * | 11/1998 | Oraevsky et al. | 600/407 |
| 5,997,481 A | | 12/1999 | Adams et al. | |
| 6,039,694 A | | 3/2000 | Larson et al. | |
| 6,132,378 A | | 10/2000 | Marino | |
| 6,139,502 A | | 10/2000 | Fredriksen | |
| 6,174,683 B1 | | 1/2001 | Hahn et al. | |
| 6,261,231 B1 | | 7/2001 | Kagan et al. | |
| 6,302,848 B1 | | 10/2001 | Larson et al. | |
| 6,676,607 B2 | * | 1/2004 | de Juan et al. | 600/461 |
| 6,689,067 B2 | * | 2/2004 | Sauer et al. | 600/464 |
| 6,837,855 B1 | * | 1/2005 | Puech | 600/452 |
| 6,949,071 B1 | * | 9/2005 | Saied et al. | 600/445 |
| 2001/0029335 A1 | * | 10/2001 | Juan et al. | 600/437 |
| 2002/0068871 A1 | * | 6/2002 | Mendlein et al. | 600/459 |

* cited by examiner

Figure 1. Perspective drawing of the ultrasound transducer interface
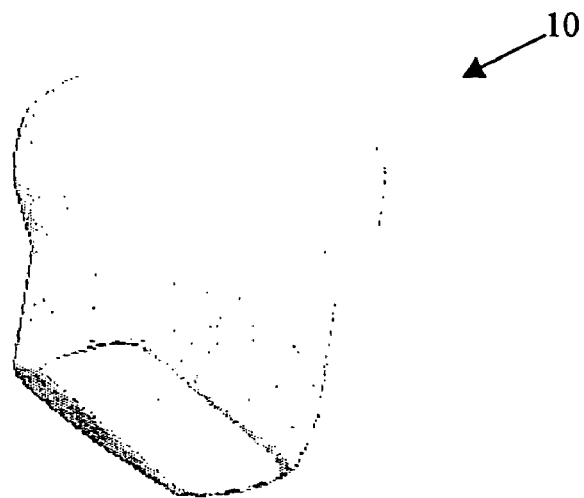
Figure 2. Cross-section drawing of interface device
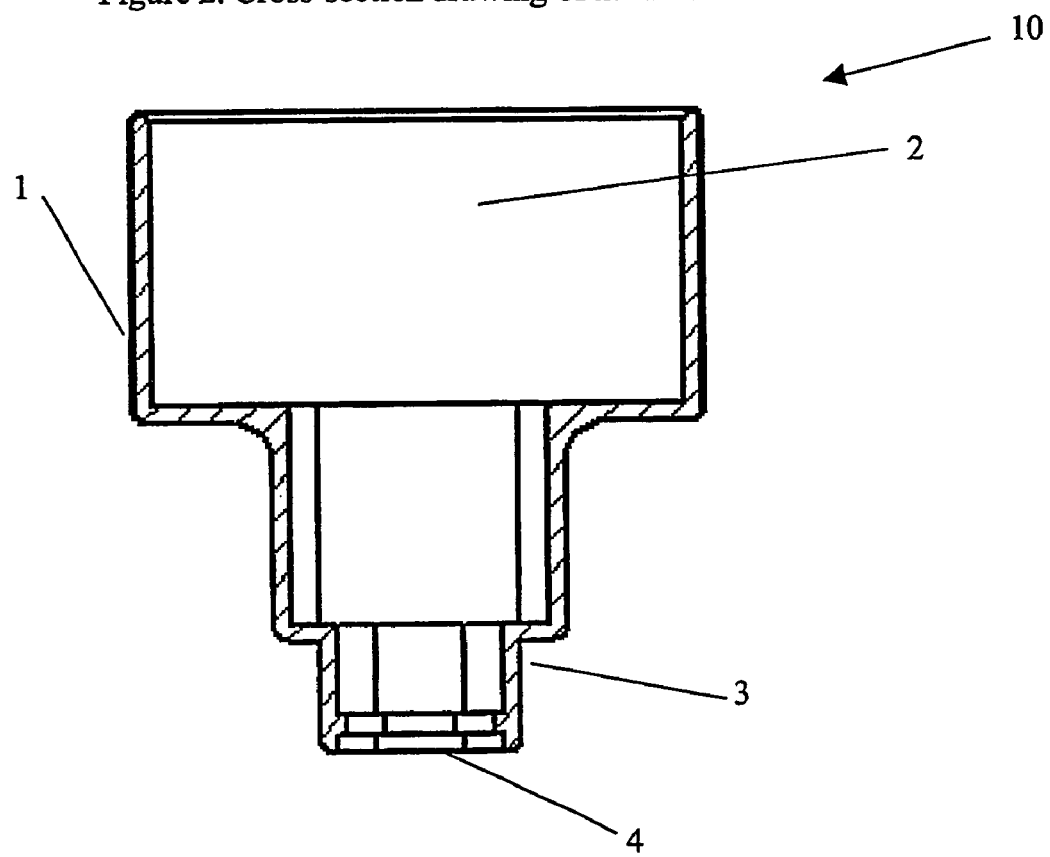

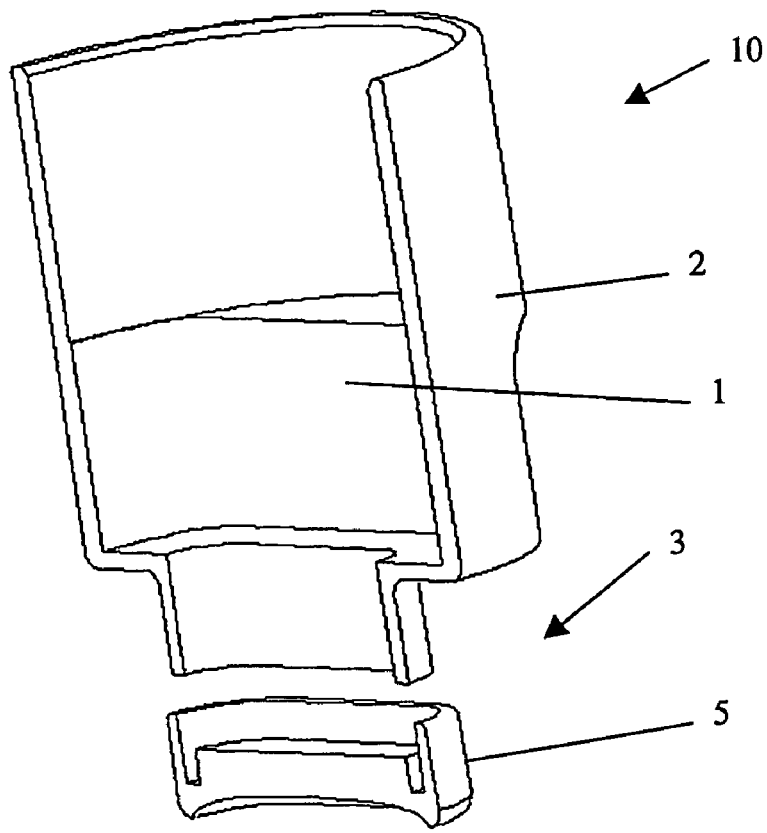
Figure 3. Cross-Sectional view of device with molded window component.

ULTRASOUND INTERFACING DEVICE FOR TISSUE IMAGING

BACKGROUND OF INVENTION

Ultrasound imaging is routinely used in medicine for non-invasive imaging of tissues and organs, both for diagnosis and for image guided surgery. The resolution of ultrasound imaging is inherently limited by the frequency of the ultrasound used, with higher frequency providing higher resolution but at the expense of reduced tissue penetration. The most common forms of medical ultrasound imaging, cardiac and fetal imaging, utilize ultrasound frequencies in the range of approximately 2 to 10 Megahertz (MHz) in order to image deep tissues. The ultrasound transducers used in general imaging are typically phased array designs, with a plurality of fixed transducer elements used to form a scan head of a probe. The individual transducer elements are switched electronically to sweep the ultrasound beam across an area to be imaged at high frame rates.

High frequency ultrasound imaging, generally in the range of 50 to 100 MHz, is used to obtain images of smaller structures requiring higher resolution than standard imaging. However with high frequencies, it is technically difficult to fabricate a phased array of transducer elements due to the small wavelengths and resultant precision and small size required of the array. Typically, a high frequency ultrasound system scan head consists of a single element transducer, which is moved mechanically with high precision across the area to be imaged. Such methods of mechanical scanning were commonly used in low frequency ultrasound imaging prior to the development of phased array methods.

In ultrasound imaging, the transducer must transmit and receive the ultrasound signals through an appropriate medium, acoustically coupled to the tissue surface of the body area of interest. Ultrasound is highly reflective from a gas interface, therefore the coupling medium must be a solid, liquid or gel substance with the appropriate acoustic properties. The coupling medium must create a continuous acoustic path between the transducer and the body of interest without any entrapped gas, with minimal attenuation and minimal reflectivity of the signal. High frequency single element transducers usually incorporate one or more acoustic matching layers on the face. The matching layer allows the signal to be transmitted from the acoustic element, a material with high acoustic impedance, into a media of much lower impedance, such as water or tissue. The coupling materials between the transducer's matching layers and the tissues are desired to have acoustic impedance characteristics similar to that of tissues, with low attenuation and scattering at the ultrasound frequencies utilized to obtain the best possible signals for imaging. A wide range of plastics, rubbers, and gels are effective at the low frequencies used in general imaging. Common low frequency ultrasound scanners usually employ a urethane polymer covering. A flowable, viscous coupling gel is applied to the covering and to the patient to complete the acoustic pathway. However, ultrasound attenuation and scattering properties increase with frequency. The requirements for materials to interface between the transducer and a tissue surface become more stringent with high frequency ultrasound imaging. In ranges at and above 50 MHz, most commonly used coupling materials are no longer acceptable.

High frequency ultrasound is particularly useful in imaging the eye due to the small dimensions of the associated tissue structures and the relative lack of imaging depth required. Currently available ophthalmic ultrasound scanners use frequencies of approximately 50 MHz to image the eye, with a single element transducer mechanically scanned over the area to be imaged. Typical scanners require that the eye have an eyecup placed around its perimeter and filled with water to acoustically couple the ultrasound signals from the transducer directly to the tissue surface.

However, the use of an eyecup is cumbersome, uncomfortable to the patient, and limits the use of ultrasound imaging during surgical procedures due to the difficulty in maintaining a sterile field and the inconvenience of having to apply the cup when images are required. Imaging systems configured in this manner also represent a serious risk to the patient as there is no barrier between the moving transducer and the surface of the eye.

U.S. Pat. No. 4,483,343 to Beyer et al., entitled "Ultrasonic Applicator" Nov. 20, 1984, describes an ultrasonic applicator system using a liquid containing sack, which is coupled to the transducer element or elements. The liquid containing sack may be adjusted in height and applied to a body surface under examination.

U.S. Pat. No. 4,649,925 to Dow et al., entitled "Ultrasonic Transducer Probe Drive Mechanism with Position Sensor" Mar. 17, 1987, describes a mechanical scan drive mechanism for an ultrasound probe with a cap over the imaging end, described to be made of polyethylene or other material, which is highly transmissive to ultrasound.

U.S. Pat. No. 4,722,346 to Chen, entitled "Stand-Off Device with Special Fluid" describes a standoff device for use with acoustic transducers in which a chamber having a diaphragm portion containing a liquid acts as the coupling medium.

U.S. Pat. No. 4,796,632 to Boyd et al., entitled "Standoff Adapter for Ultrasound Probe" Jan. 10, 1989, describes an adapter and standoff for an ultrasound probe comprising a molded elastic coupler that is filled with fluid to act as the acoustic coupling medium.

U.S. Pat. No. 5,078,149 to Katsumata et al., entitled "Ultrasonic Coupler and Method for Production Thereof" Jan. 7, 1992, describes an ultrasonic coupler provided with an acoustic coupling medium formed of a water containing polymeric gel produced by integrally cross-linking an aqueous solution of water-soluble polymeric compound, and a holder for accommodating the coupling medium.

U.S. Pat. No. 5,626,554 to Ryaby et al., entitled "Gel Containment Structure" May 6, 1997, describes a gel containment structure, a bladder that is used to conform to the body surface for the application of ultrasound.

U.S. Pat. No. 5,770,801 to Wang et al., entitled "Ultrasound Transmissive Pad" Jun. 23, 1998, describes a pad for transmitting acoustical waves between an ultrasound probe and a target surface. The pad includes a first porous layer and a second porous layer with an ultrasound couplant such as water, glycerin, or silicone oil disposed between the layers.

U.S. Pat. No. 5,997,481 describes a probe cover for an ultrasound imaging probe, the cover including a reservoir for containing a quantity of ultrasonically transmissive gel. U.S. Pat. No. 6,039,694 to Larson et al., entitled "Coupling Sheath for Ultrasound Transducers" Mar. 21, 2000, describes a homogenous, solid, elastic, biocompatible sheath that is conformal to the ultrasound transducer. The sheath is described to be comprised of about 20 to 95% biocompatible liquid, such as water or saline, resulting in a desirable level of acoustic coupling, with acceptable low levels of acoustic artifacts, distortion and attenuation, and provides a microbial barrier between the transducer and surgical field or skin.

U.S. Pat. No. 6,132,378 to Marino, entitled "Cover for Ultrasound Probe" Oct. 17, 2000, describes a cover for an ultrasound probe that is a cup-like device that fits over the probe. A membrane comprising two polyurethane sheets with gel disposed between them is attached to the base of the cup to act as the acoustic coupling medium between the probe and the tissue surface against which the membrane is placed.

U.S. Pat. No. 6,139,502 to Fredriksen, entitled "Ultrasonic Transducer Probe and Handle Housing and Stand-Off Pad" Oct. 31, 2000, describes an ultrasonic transducer probe and handle housing to which a stand-off pad may be affixed to the base and may be adapted to contain a fluid.

U.S. Pat. No. 6,302,848 to Larson et al., entitled "In Vivo Biocompatible Acoustic Coupling Media" Oct. 16, 2001 describes a medical ultrasound coupling medium and lubricant in gel or liquid form, comprised of polyethylene oxide and aqueous solvent solutions.

OTHER KNOWN PATENT REFERENCES

U.S. Pat. No. 3,939,123 entitled "Lightly Cross-Linked Polyurethane Hydrogels Based on Poly(alkylene ether) Polyols" to Matthews, et al., Feb. 17, 1976.

U.S. Pat. No. 4,118,354 entitled "Polyurethane Hydrogel and Method for Production of Same" to Harada, et al., Oct. 3, 1978.

U.S. Pat. No. 4,209,605 entitled "Process for Producing Shaped Polyurethane Hydrogel Articles" to Hoy, et al., Jun. 24, 1980.

U.S. Pat. No. 4,644,033 "Polyurethane Hydrogels and Process for Their Manufacture" to Gnanou, et al., Feb. 17, 1987.

U.S. Pat. No. 5,175,229 entitled "Biocompatible Polyurea-Urethane Hydrated Polymers" to Braatz, et al., Dec. 29, 1992.

U.S. Pat. No. 6,174,683 entitled "Method of Making Biochips and the Biochips Resulting Therefrom" to Hahn, et al., Jan. 16, 2001.

SUMMARY OF THE INVENTION

The present invention is a device to acoustically couple a high frequency ultrasound transducer to the surface of the tissues to be imaged. The device provides an acoustic pathway of minimal effect on the ultrasound signals. The device may be directly placed on the tissue region to be imaged to act as a standoff and aid in placing the desired tissue region into the focal zone of the ultrasound beam. The device may be provided in a sterile, replaceable form to prevent contamination of the field and allow for the use of ultrasound imaging during surgery. Furthermore, the device provides a safety barrier between the moving transducer and the tissues being imaged. The invention is especially useful in the application of high frequency ultrasound for diagnosis and surgical treatment of the eye.

BRIEF DESCRIPTION OF THE DRAWINGS

FIG. 1 is a perspective view of the ultrasound transducer interface.

FIG. 2 is a cross-sectional view of the ultrasound transducer interface.

FIG. 3 is a cross-sectional view of the device with molded scan window component.

DESCRIPTION OF INVENTION

The invention is an interface device 10 placed between a high frequency ultrasound transducer and a tissue surface being imaged, which allows high frequency ultrasound imaging with minimal acoustic interference and artifacts. The device 10 is configured for use with a mechanically scanned system, which typically uses a single transducer with a fixed focus traversed across a path or arc. The device 10 may also be used or modified to be used with other systems. The configuration of the device 10 allows it to function as a standoff for the ultrasound transducer to place the focus of the ultrasound beam at the desired depth of tissue for imaging. In addition, the device 10 may be sterilized and replaced as needed, providing sterile tissue contact surfaces. The device 10 has additional features, which are especially advantageous for diagnosis and surgery of the eye.

The device 10 comprises a fluid containing reservoir 1 with a proximal 2 and a distal 3 end, the proximal end 2 interfacing to a scan head containing a transducer. The distal end 3 interfaces to a tissue surface at a region to be imaged. The reservoir 1 is open at the proximal end 2 and is sized to allow a mechanically scanning transducer to traverse the desired range of scan motion while within the proximal end 2 of the reservoir 1. The reservoir 1 extends in length below the distal end of the transducer through its range of motion to prevent contact of the tissue surface with the moving transducer. The distal end 3 consists of a scan window 4 through which the ultrasound beam passes through to interrogate the tissue in the scan region. The scan window 4 is formed of a material highly transparent to high frequency ultrasound, and also provides a seal to the fluid coupling media disposed within the reservoir 1. By mounting the proximal end 2 of the device 10 to the scan head by fluid tight means, the transducer is sealed in the reservoir 1, and the scan head may be placed in any orientation for ultrasound imaging.

Typically the focal length of the transducer extends past the length of the reservoir 1 and scan window 4, into the tissue region of interest. Due to the greater resolution provided by high frequency ultrasound transducers at the focus, it is important to set the length of the device 10 to position the focus at the desired tissue depth. For high frequency ultrasound imaging of the anterior segment of the eye, an imaging depth of 2 to 6 mm past the distal tip of the device 10 is preferred. The overall length of the device 10 must be stable during use so that precise control of the focal depth is provided and motion artifacts are not introduced.

The exact shape of the proximal end 2 of the reservoir 1 is constrained to tightly enclose the scan motion of the transducer. With a simple toggle scan motion of the transducer, the reservoir 1 cross-section may be circular, oval, or rectangular. For more complex orbital or arc scanning motions, the geometry is more complicated, being some portion of a strip on a sphere that extends within a set of latitude and longitude limits. The essential principle of the invention can apply to accommodate these more complex forms of transducer motion. The cross-section of the distal end 3 of the reservoir 1 is shaped to enclose the transmitted and received ultrasound signals. The distal end 3 cross-section is typically smaller than that of the proximal end 2, allowing the reservoir 1 to have a cross-section tapered toward the distal end 3. The scan window 4 is typically larger than the ultrasonic beam width at that plane to prevent reflections from the side walls and edges.

The reservoir 1 may be fabricated from any material with sufficient structural integrity and impermeability to the fluid contained within the reservoir 1. Preferably, the reservoir 1 comprises a polymer, such as a thermoplastic or rubber. Clear materials are preferred to allow the user to view the tissue area being scanned. Suitable polymers of construction include, but are not limited to, nylon, polyvinyl chloride, polycarbonate, polyethylene, polyurethane, polysiloxanes, polysulfone, polystyrene, polymethylmethacrylate, polypropylene, polyacrylics, and their copolymers. Preferred embodiments include those materials that may be sterilized by ionizing radiation. The reservoir 1 may include two or more parts so that the scan window 4 may be mechanically secured between two or more parts. In addition, the use of multiple parts for the reservoir 1 may allow adjustability in the overall length of the reservoir 1, and thereby allowing adjustment of the position of the transducer focus in the underlying tissue. The distal edges of the reservoir 1 are preferred to comprise a sufficiently soft material to prevent tissue damage, especially to sensitive areas of anatomy such as the eye, while maintaining structural integrity.

The proximal end 2 of the reservoir 1 may be attached to the scan head containing the transducer through a variety of mechanical means including screw threads, interference fit, compression ring, or bayonet mount. The proximal end 2 may incorporate a circumferential rubber component to facilitate a fluid tight seal such as an O-ring or a rubber bellows to surround the transducer and allow transducer motion. The attachment of the proximal end 2 of the device 10 to the scan head may incorporate adjustment of the length of the device 10 extending distal to the transducer, such as with a screw mechanism. The ability to adjust this length allows the position of the focus of the transducer beneath the tissue surface to be adjusted, or to adjust for transducers having different focal lengths.

The scan window 4 is formed of a material with low acoustic attenuation, approximating the acoustic characteristics of soft tissue. The material should have low scattering and reflectivity at ultrasound frequencies in the range of 50 to 150 Mhz. The material should have the appropriate mechanical and toxicological properties for contact with sensitive tissues such as the surface of the eye. The material should also exhibit good shelf life properties and preferably be able to be stored at room temperature once sterilized. Depending on the frequency and on the degree of attenuation that may be compensated for by the imaging system, suitable materials include, but are not limited to, membranes of polyurethane, polymethylpentene, polysiloxane, polyisoprene, and other synthetic rubbers. Preferred are scan window materials with a hydrated tissue contacting surface. The scan window material may inherently contain water, or alternatively be surface treated to have a hydrophilic surface. At very high frequencies above 50 MHz, the material properties become more stringent and materials with high water content are preferred. Preferred materials such as non-flowable hydrogels have low attenuation to high frequency ultrasound and a high bound water content. Structurally stable hydrogels may be utilized as a membrane component of the scan window 4 or alternatively as a molded part 5. Suitable hydrogels materials include, but are not limited to, polyhydroxyethylmethacrylate, polyethylene oxide, polypropylene oxide, polyacrylic acids, polyvinylpyrolidone, cellulose and their chemical derivatives, polysaccharides, polyacrylamide and its copolymers, polyvinylalcohol, polyurethanes and hydrophilic biopolymers such as hyaluronic acid, gelatin, and alginate. Crosslinked hydrogels from such compounds may be formulated to provide a high water content to minimize attenuation, but sufficient polymer structure for mechanical integrity of the scan window 4. A mesh or porous structure may also be incorporated into the hydrogel construction to provide greater structural integrity and tear resistance. Typically, attenuation of a hydrogel increases with decreasing water content. Water contents of 80% or greater are desired to minimize attenuation and reflectivity to high frequency ultrasound.

Preferred for the scan window 4 are hydrogels that may be sterilized by ionizing radiation. Many hydrogel formulations react to form gas when subjected to radiation. The entrapment of gas bubbles in a hydrogel would render it acoustically unsuitable for use as a scan window 4 component.

A preferred polymer system for the scan window 4 is iso-cyanate terminated poly(alkylene ether) polyols. Such polymers may be formulated to form solid polyurethane hydrogels of very high water content, 80% and greater, while retaining mechanical integrity. By formulating the pre-polymers with relatively low molecular weight poly(alkylene ether), such as 1,000 to 4,000 MW, the low viscosity pre-polymers may be activated to crosslink into a variety of shapes and forms. In one embodiment, the polymer system is cast within the reservoir 1 to form the scan window 4 in place. The reservoir distal end 3 may have mechanical features to facilitate attachment of the scan window 4 material to the reservoir 1 body.

The surface of the scan window 4 interfacing the tissue surface may be concave, convex or flat as appropriate for the formation and retention of an acoustic coupling between the hydrogel and the tissue surface. Flat and concave surfaces are useful in maintaining a meniscus of coupling fluid between the device 10 and the tissues. The hydrogel may be flush with the distal edges of the reservoir 1 or may extend past the reservoir 1. Due to the high water content of a hydrogel scan window 4, the distal portion of the device 10 may be placed directly on a tissue surface providing no air is trapped under the window 4.

It is useful to have a flowable secondary coupling fluid or gel between the scan window 4 and the tissue. Typically, a flowable secondary coupling fluid or gel is applied to the tissue interface end of the device 10 to remove any entrapped air, complete the acoustic coupling with the tissue and provide a lubricating layer to allow safe movement of the device 10 over the tissue surface. Materials such as water, balanced salt solutions, artificial tear solutions, and dry eye formulations are useful in providing the final coupling of the device 10 to the eye. The system may be adapted for the manual or automatic replenishment of a secondary coupling media to the interface, such as by an attached syringe, dropper, drip tube, squeeze tube or other means.

Preferred for imaging of the eye are shapes and materials for the distal end 3 of the device 10 that facilitate the formation of a fluid meniscus between the scan window 4 and the eye to allow ultrasound scanning with minimal application of pressure to the tissues in the scan region. The eye surface is curved corresponding to a radius of approximately 8 to 13 mm. A matching concave curve on the distal end 3 of the device 10 to match the curvature of the eye surface may aid use on the eye.

The fluid within the reservoir 1 between the moving transducer and the scan window 4 is also selected for low attenuation properties to high frequency ultrasound. Suitable fluids include, but are not limited to, water, saline, silicone fluids, and glycerine solutions. The reservoir 1 should be sufficiently filled with fluid to couple the transducer to the scan window 4 throughout the range of scan motion of the transducer. Sufficient fluid level to allow orientation of the scan head in any position and to minimize foam formation is preferred. Antifoaming additives to minimize foam generation during high speed scan motion of the transducer may also be incorporated into the fluid. Due to the potential use of the device 10 on sensitive tissues such as the surface of the eye, non-toxic and non-irritating fluids are preferred. The device 10 may also incorporate fluid delivery means either to the reservoir 1 interior to make up for small fluid loss through the scan window 4, or to the distal end 3 of the device 10 to act as a coupling media and lubricant for the tissue.

The distal end 3 of the reservoir 1 may also extend past the scan window 4. The reservoir 1 may contain openings or windows to allow access of surgical tools such as needles, scalpels, guidewires, trocars and the like. If the openings are in the fluid containing portion of the reservoir 1, means to maintain a fluid seal are incorporated, such as screw threads, interference fit, compression ring, bayonet mount, O-ring, a rubber bellows etc. Surgical tools may be incorporated into or onto the device 10 to allow positioning of the tools in tissue in relation to the displayed image. A variety of configurations including surgical tools are consistent with the scope of the invention.

The entire device 10 is preferably sterilizable for use. The device 10 may be easily removed and replaced for each patient. All materials of construction are preferred to be stable to sterilization by ionizing radiation, such as gamma or electron beam irradiation. The device 10 is preferred to be packaged singly in a sterile container. Embodiments incorporating a hydrogel scan window 4 are preferred to be packaged in a hydrated state.

EXAMPLES

Example 1

Fabrication and Testing of Ultrasound Interfacing Devices

Various materials were prepared as films and investigated to determine suitability for use as a scan window for high frequency ultrasound imaging. Each material sample was fixed in a machined Delrin cap and attached to the scan head of a high frequency ultrasound handpiece. The ultrasound imaging system was set up with a flat plate target at the focal distance of the ultrasound transducer. The system operated at a center frequency from 50-70 MHz. The samples were imaged under the same conditions and were evaluated for surface reflectivity, reverberations, and attenuation of the ultrasound signal. The following table lists the materials and conditions.

| Material | Condition |
| --- | --- |
| Urethane/Silicone Copolymer—Elasteon, Aortech Intl | Shore 80A, 125 micron thick film |
| Silicone RTV—General Electric | Cast film from solvent dispersed RTV, ~650 micron thick |
| Silicone RTV-L Silastic—Dow Corning | Cast film from solvent dispersed RTV, ~650 micron thick |
| PolyHEMA (polyhydroxyethylmethacrylate) - Sigma Aldrich | Cast film from 12% in ethanol ~75-100 micron thick, ~40% polymer, 60% water content |
| 1.0% Agar—Sigma Aldrich (99% water content) | Poured gel ~2 mm thick |
| 1.5% Agar—Sigma Aldrich (98.5% water content) | Poured gel ~1 mm thick |
| 1.5% Gelatin—Woburn (98.5% water content) | 225A Bloom, Poured gel ~1 mm thick |
| 5.0% Gelatin—Woburn (95% water content) | 225A Bloom, Poured gel ~1 mm thick |
| 1.0% Alginic Acid, Hi viscosity- Sigma Aldrich | Cross linked with $CaCl_2$, gel ~1 mm thick |
| 2.5% Alginic Acid, Lo viscosity- Sigma Aldrich | Cross linked with $CaCl_2$, gel ~1 mm thick |
| 4% Polyurethane Hydrogel—Biocept Inc. | Isocyanate cross-link, gel ~1-2 mm thick |
| 5% Polyurethane Hydrogel—Biocept Inc. | Isocyanate cross-link, gel ~1-2 mm thick |
| 8% Polyurethane Hydrogel—Biocept Inc. | Isocyanate cross-link, gel ~1-2 mm thick |
| 10% Polyurethane Hydrogel—Biocept Inc. | Isocyanate cross-link, gel ~1-2 mm thick |
| 12% Polyurethane Hydrogel—Biocept Inc. | Isocyanate cross-link, gel ~1-2 mm thick |

The urethane/silicone copolymer, silicone and polyHEMA films, all showed very high surface reflectivity and varying but significant amounts of attenuation. The highly reflective surfaces tended to saturate the return signal to the system and create reflections at lower imaging depths. The water weight % of the hydrogels was estimated as [100%-polymer weight %]. The water weight % of the polyHEMA was measured by comparing dry and wet samples. All of the high water content hydrogel materials had very low surface reflectivity and corresponding low attenuation of 2 dB or less. In the case of the polyurethane hydrogel (Biocept Inc., Carlsbad, Calif.), signal loss was seen to increase with increasing polymer concentrations.

Example 2

Ultrasound Characterization of Scan Window Material Candidates

Ultrasound signal loss and time-of-flight characteristics were measured on candidate scan-window polymer samples. These quantities were measured with respect to a 2-way flat plate impulse response with a water-only path.

The test system for measuring the signal loss consisted of: a Tektronix TDS 544A oscilloscope, Panametrics 5910R Pulser-receiver, a high frequency ultrasound transducer with a 62 MHz center frequency, 6 mm focal length and approximately 45% bandwidth, and a fused silica flat plate target. All measurements were taken with 50 dB of attenuation on the Panametrics receiver. The samples were placed at a distance approximating where they would be if used as a scan window located 4 mm away from the transducer face or 2 mm away from the nominal focus. An impulse response was first maximized without any sample by obtaining peak signal amplitude by varying the depth and target angle. The 64× average peak-to-peak voltage and the time delay were recorded. Each sample was placed in the ultrasound path on the 2 mm platform above the target and the amplitude and delay were recorded for each sample. Between each sample, the "no-sample" reference amplitude and delay were checked and recorded to ensure standard conditions. Additionally, waveforms were recorded for each sample and the reference signal.

The calculation for signal loss and time of flight did not compensate for the water attenuation or any other causes of lost signal, but simply took the loss of signal with respect to the reference signal. The signal loss was calculated from 20*log[sample amplitude/reference amplitude]/(2*thickness). The velocity was calculated from the differences in the time-of-flight using the formula: velocity=thickness/{delay w/sample−[delay w/o sample−(thickness/Vw)]}. Vw is the speed of sound in water, approximately 1.5 mm/uS.

Before the material samples were measured for signal loss, thickness measurements were made. Samples with low compressibility were measured using a dial thickness gauge. Due to deformation of the hydrogels during measurement with a dial thickness gauge, the hydrogels were measured using a high frequency ultrasound imaging system. The polyHEMA film thickness was measured dry and hydrated thickness calculated based on water content. The hydrogel samples were faced convex side down and allowed to float to the bottom of a petri dish. The petri dish distance was gauged right next to each sample. The transducer was positioned to the point where the sample was flattest and touching the bottom of the plate, enabling the thickness to be measured using only the echo off the top surface.

Results:

| Polymer Type | Signal Loss [dB/mm] |
| --- | --- |
| 50% Polyurethane Hydrogel (Biocept, Inc.) | 0.88 |
| 20% Polyurethane Hydrogel (Biocept, Inc.) | 0.57 |
| 15% Polyurethane Hydrogel (Biocept, Inc.) | 0.53 |
| 10% Polyurethane Hydrogel (Biocept, Inc.) | 0.33 |
| 5% Polyurethane Hydrogel (Biocept, Inc.) | 0.23 |
| 15% Gelatin | 0.63 |
| 10% Gelatin | 0.40 |
| 5% Gelatin | 0.09 |
| polyHEMA (40% polymer, 60% water) | 10.62 |
| CarboSil-20 (Polymer Technology Group Inc.) | 104.94 |
| PurSil-20 (Polymer Technology Group Inc.) | 94.81 |
| PurSil Al-20 (Polymer Technology Group Inc.) | 80.95 |
| TPX (Polymethylpentene, Mitsui Chemicals Inc.) | 26.68 |
| Polydimethylsiloxane (Nusil Med6210) | 42.48 |
| Polyurethane (Pellethane, Dow Chemical Co.) | 63.91 |
| Polyimide (Imidex, Mitsui Chemicals Inc.) | 49.19 |
| Polyetherimide (Tempalux, Westlake Plastic Co.) | 44.30 |

Example 3

Sterilized Ultrasound Interfacing Device

Ultrasound interfacing devices were fabricated for use with the high frequency ultrasound imaging system described above. The devices were formed of machined nylon 66 caps designed to attach to the distal end of the scanhead. The distal end of the device was a rectangular window opening for the imaging hydrogel, the opening being 4 mm×9 mm in dimension. The distal segment of the device was designed to provide for mechanical entrapment of the gel by use of contours on the interior surface.

Polyurethane hydrogel scan windows were cast into the devices in varying polymer concentrations and used for imaging on ex-vivo and in-vivo human eyes. The polyisocyanate prepolymer was diluted with acetonitrile to concentrations of 20%, 15% and 10% by weight. A solution of 50 mM sodium bicarbonate was prepared and adjusted to a pH in the range of 7.6-7.8. The prepolymer solutions were mixed with the bicarbonate solutions in a 1:1 ratio to yield final solutions of 10%, 7.5% and 5% by weight. The aqueous solution initiated the cross-linking reaction for the hydrogel, while the acetonitrile solvent controlled the reaction to prevent foam formation.

The devices were placed on specially prepared glass plates incorporating silicone rings to hold the device distal end and provide a fluid dam to prevent loss of prepolymer solution upon casting. Upon final mixing, prepolymer solution was pipetted into the cap's distal end to a depth of 1-3 mm. The prepolymer solution polymerized to form a firm hydrogel in approximately 15 minutes. The devices were placed in sealed containers with water in the containers to maintain high humidity during curing. The hydrogel samples were allowed to cure for 24 hours.

After curing, the devices were washed in deionized water 3 times for a period of 60 minutes each. The devices were placed onto pre-cut polystyrene holders to prevent movement during transport. The holders were then placed into sterile specimen containers with sealed lids along with approximately 20 ml of DI water to maintain humidity. The containers were sealed into sterilization peel pouches. The packaged devices were sterilized using E-beam sterilization with a dosage of 15-17 KGy. Although slight yellowing of the nylon reservoir material was noted, the hydrogel scan windows did not exhibit any significant change and were found to be acoustically suitable for high frequency ultrasound imaging.

The sterilized devices were used to perform imaging on both ex-vivo and in-vivo human eyes. In order to facilitate coupling of the hydrogel to the eye, an aqueous solution was used. In various trials, distilled water, artificial tear solutions, lubricant eye drops (carboxymethylcellulose 1.0% and hydroxypropyl methylcellulose 5.0%) were used. The higher viscosity solutions were found to be the most efficacious at maintaining a lasting fluid meniscus between the eye and the hydrogel scan window. All of the hydrogel formulations imaged well with minimal surface reflectivity and attenuation. The 5% hydrogel was fairly soft and tended to distort in shape upon full hydration before use. The 7.5% and 10% hydrogels presented good consistency and imaging characteristics. No ocular irritation was noted by the subjects during in-vivo imaging.

Example 4

Ultrasound Interfacing Devices with Support Structure Incorporated into Scan Window High-water content, low polymer concentration hydrogels as detailed in Example 1 may not have the structural integrity to withstand storage, transport and use in many situations. A variety of hydrogel scan window samples were created with structural reinforcement in order to provide for the stability required for durability. A series of square looms approximately 1.5 inches on a side were fabricated. The loom frames had holes every 0.1" along the sides. Acrylic monofilament 0.005" diameter was run in a crossing pattern to create an open mesh. Polyurethane hydrogel in concentrations of 4% and 5% was prepared as in example 3 and cast into the looms and allowed to cure for 24 hours. As an alternate design, a section of porous polyethylene tubing, 0.5" inner diameter with pore size of approximately 250 microns was used as the frame member and monofilament strung across one end to create a mesh. A 4% polyurethane hydrogel was cast into the end of the tube, to a depth covering the mesh.

Imaging was performed on the reinforced samples, with both flat-plate and ex-vivo human eyes. The reinforced hydrogels all exhibited good imaging qualities. The mesh could be seen when examining the near-field image but did not substantially affect the image quality unless the mesh was moved closer to the target. In the far field, the mesh was highly reflective and exhibited some reverberations, as well as some shadowing underneath. Varying the spacing of the mesh may also be used to decrease the effects.

Many features have been listed with particular configurations, options, and embodiments. Any one or more of the features described may be added to or combined with any of the other embodiments or other standard devices to create alternate combinations and embodiments.

Although the examples given include many specificities, they are intended as illustrative of only a few possible embodiments of the invention. Other embodiments and modifications will, no doubt, occur to those skilled in the art. Thus, the examples given should only be interpreted as illustrations of some of the preferred embodiments of the invention, and the full scope of the invention should be determined by the appended claims and their legal equivalents.

What is claimed is:

1. An interface device for use with an ultrasound imaging system having a scan head with at least one transducer, the interface device being removably attachable to the scan head, the interface device comprising:
    a reservoir with a proximal end and a distal end, said proximal end being open and shaped to allow the transducer to be inserted within said reservoir, wherein said proximal end of said reservoir is configured to maintain a fluid tight seal between said reservoir and the scan head, and wherein said distal end of said reservoir is configured to extend past a distal end of the transducer,
    a scan window located proximate said distal end of said reservoir through which ultrasound energy is transmitted and received, wherein said scan window is formed of a solid, non-flowable hydrogel,
    a fluid tight seal between said scan window and said distal end of said reservoir,
    and a fluid acoustic coupling medium located within said reservoir and filling a space between said transducer and said scan window,
    wherein said solid, non-flowable hydrogel comprises a cross-linked hydrogel and wherein said scan window further comprises a support structure comprising a mesh of filaments embedded in the cross-linked hydrogel.

2. The interface device of claim 1, wherein the interface device is sterile.

3. The interface device of claim 2, wherein the interface device is constructed of materials suitable to be sterilized by ionizing radiation.

4. The interface device of claim 1, wherein said scan window is formed of a material with less than 1 dB/mm signal loss of transmitted and received high frequency ultrasound at a frequency in a range of 50 to 100 MHz.

5. The interface device of claim 1, wherein the scan window comprises a cross-linked hydrogel.

6. The interface device of claim 5, wherein said cross-linked hydrogel comprises a cross-linked polymer with water content greater than or equal to 50% by weight.

7. The interface device of claim 5, wherein said cross-linked hydrogel comprises polyethylene oxide.

8. The interface device of claim 5, wherein said cross-linked hydrogel is formed from polyisocyanate terminated poly(alkylene ether) polyols.

9. The interface device of claim 1, wherein reservoir has an adjustable length for adjusting a distance between the scan window and the transducer.

10. The interface device of claim 9, wherein the distance between said scan window and the transducer is adjustable to position the transducer focus approximately 2 to 6 mm distal to said scan window.

11. The interface device of claim 1, wherein a distal surface of said scan window has a preformed concave curve to approximate a curvature of an eye.

12. The interface device of claim 1, wherein the reservoir comprises a plurality of separate pieces between which said scan window is mechanically secured.

13. The interface device of claim 1, wherein the device incorporates delivery of fluid acoustic coupling material to a distal surface of said scan window.

14. The interface device of claim 1, wherein the interface device is configured to be removably attachable to the scan head of a high frequency ultrasound imaging system operable at a frequency in a range of 50 to 100 MHz.

15. The interface device of claim 1, wherein the device incorporates access for surgical instruments.

16. The interface device of claim 1, wherein the device incorporates a surgical instrument.

17. The interface device of claim 1, wherein the device incorporates a surgical instrument that allows use of the instrument in positional relationship to the scanned image.

18. The interface device of claim 1, wherein said proximal end of said reservoir is configured to allow the transducer to traverse across an intended scan path within said reservoir.

19. The interface device of claim 1, wherein the scan window comprises a cross-linked hydrogel and a mesh support extending across the scan window.

20. The interface device of claim 1, wherein said mesh of filaments is in a crossing pattern embedded in the cross-linked hydrogel.

21. An interface device for use with an ultrasound imaging system having a scan head with at least one transducer, the interface device being removably attachable to the scan head, the interface device comprising:
    a reservoir with a proximal end and a distal end, said proximal end being open and shaped to allow the transducer to be inserted within said reservoir, wherein said proximal end of said reservoir is configured to maintain a fluid tight seal between said reservoir and the scan head, and wherein said distal end of said reservoir is configured to extend past a distal end of the transducer,
    a scan window located proximate said distal end of said reservoir through which ultrasound energy is transmitted and received, wherein said scan window is formed of a solid, non-flowable hydrogel,
    a fluid tight seal between said scan window and said distal end of said reservoir,
    and a fluid acoustic coupling medium located within said reservoir and filling a space between said transducer and said scan window,
    wherein the reservoir has an adjustable length for adjusting a distance between the scan window and the transducer,
    and wherein said solid, non-flowable hydrogel comprises a cross-linked hydrogel and wherein said scan window further comprises a support structure comprising a mesh of filaments embedded in the cross-linked hydrogel.

22. An interface device for use with an ultrasound imaging system having a scan head with at least one transducer, the interface device being removably attachable to the scan head, the interface device comprising:
    a reservoir with a proximal end and a distal end, said proximal end being open and shaped to allow the transducer to be inserted within said reservoir, wherein said proximal end of said reservoir is configured to maintain a fluid tight seal between said reservoir and the scan head, and wherein said distal end of said reservoir is configured to extend past a distal end of the transducer, a scan window located proximate said distal end of said reservoir through which ultrasound energy is transmitted and received, wherein said scan window is formed of a hydrogel with a support structure comprising a mesh of filaments embedded in said hydrogel, a fluid tight seal between said scan window and said distal end of said reservoir, a fluid acoustic coupling medium located within said reservoir and filling a space between said transducer and said scan window.

23. The interface device of claim 22, wherein said mesh of filaments is arranged in a crossing pattern.

24. The interface device of claim 22, wherein said reservoir has an adjustable length for adjusting a distance between the scan window and the transducer.

25. The interface device of claim 24, wherein said mesh of filaments is arranged in a crossing pattern.

* * * * *